(12) United States Patent
Bell et al.

(10) Patent No.: US 10,161,903 B2
(45) Date of Patent: Dec. 25, 2018

(54) ELECTROBLOTTING DEVICE

(71) Applicant: PIERCE BIOTECHNOLOGY, INC., Rockford, IL (US)

(72) Inventors: Peter Alan Bell, South Beloit, IL (US); Surbhi Desai, Rockford, IL (US); John David Dwenger, Roscoe, IL (US); Boguslawa R. Dworecki, Rockford, IL (US); Stefan Reiley Freeman, Crystal, MN (US); Eric Leigh Hommema, Roscoe, IL (US); Gregory John Kilmer, Winnebago, IL (US); Priya Rangaraj, Rockford, IL (US); Stephen D. Shiflett, Rockford, IL (US); Hongfang Wang, Shanghai (CN); Brian Lynn Webb, Roscoe, IL (US)

(73) Assignee: PIERCE BIOTECHNOLOGY, INC., Rockford, IL (US)

( * ) Notice: Subject to any disclaimer, the term of this patent is extended or adjusted under 35 U.S.C. 154(b) by 665 days.

(21) Appl. No.: 13/770,361

(22) Filed: Feb. 19, 2013

(65) Prior Publication Data
US 2014/0231255 A1  Aug. 21, 2014

(51) Int. Cl.
*G01N 27/447* (2006.01)

(52) U.S. Cl.
CPC ............ *G01N 27/44739* (2013.01)

(58) Field of Classification Search
CPC ..... G01N 27/44739; E05C 9/02; E05C 9/185; G06F 1/1616; G06F 1/1679; G06F 1/1635; Y10T 292/08
USPC ................................................. 204/543, 627
See application file for complete search history.

(56) References Cited

U.S. PATENT DOCUMENTS

| 4,840,714 | A | | 6/1989 | Littlehales |
| 5,716,730 | A | * | 2/1998 | Deguchi .............. H01M 2/1022 429/123 |
| 8,075,755 | B2 | | 12/2011 | Yang et al. |
| 8,192,601 | B2 | | 6/2012 | Latham |
| 8,357,278 | B2 | | 1/2013 | Latham |

(Continued)

FOREIGN PATENT DOCUMENTS

CN         102325786         6/2014

OTHER PUBLICATIONS

Towbin et al. Electrophoretic transfer of proteins from polyacrylamide gels to nitrocellulose sheets: Procedure and some applications, vol. 76, No. 9, (1979), pp. 4350-4354.

(Continued)

*Primary Examiner* — Gurpreet Kaur

(57) ABSTRACT

An electroblotting system including a cassette configured to receive a membrane and a material impregnated with at least one of proteins or nucleic acids. The cassette is connectable to a base such that a current is passable through the cassette to cause at least some of the proteins or nucleic acids to be transferred from the impregnated material to the membrane. The cassette has a first portion, a second portion configured to be releasably coupled to the first portion, and a coupling mechanism configured to releasably couple the first portion to the second portion. The cassette further includes an actuator operatively coupled to the coupling mechanism such that manual depression of the actuator causes the coupling mechanism to release the first portion relative to the second portion.

17 Claims, 9 Drawing Sheets

(56) References Cited

U.S. PATENT DOCUMENTS

| | | |
|---|---|---|
| 2006/0166083 A1 | 7/2006 | Zhang et al. |
| 2011/0297544 A1 | 12/2011 | Latham |
| 2011/0297545 A1 | 12/2011 | Latham et al. |
| 2013/0258560 A1* | 10/2013 | Wang .................... G06F 1/1635 |
| | | 361/679.01 |

OTHER PUBLICATIONS

Timmons and Dunbar. Protein Blotting and Immunodetection, Methods in Enzymology, vol. 182 (1990), pp. 679-688.
Trans-Blot® Turbo™ Transfer System Transfer Pack, Bio-Rad, available at http://www.bio-rad.com/webroot/web/pdf/lsr/literature/10019593D.pdf (2011).

* cited by examiner

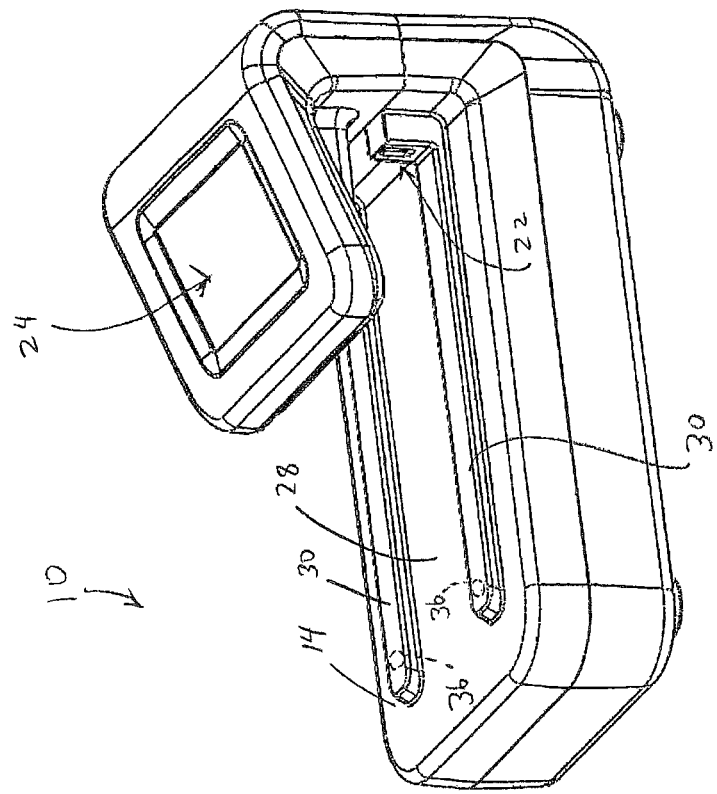
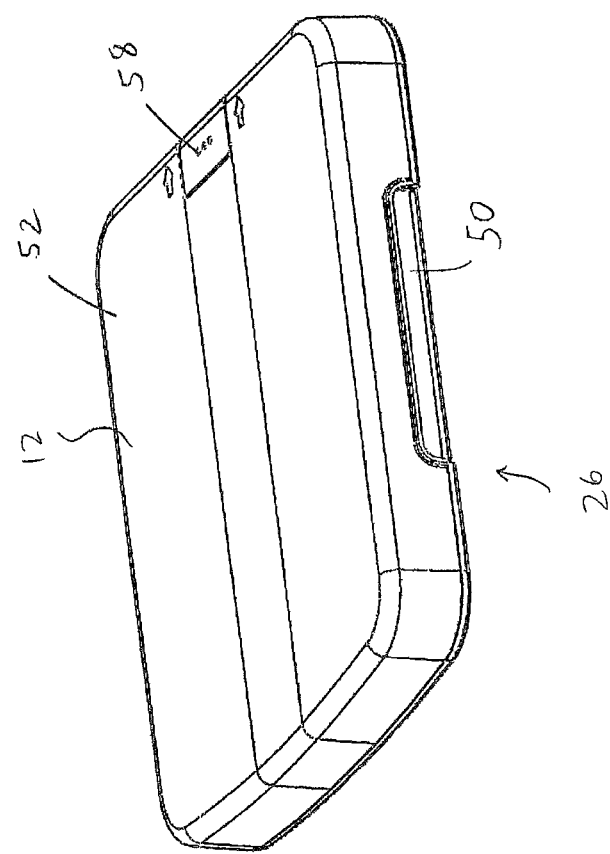
FIG. 1

ELECTROBLOTTING DEVICE

Electroblotting device for transferring proteins or nucleic acids onto a membrane.

BRIEF DESCRIPTION OF THE DRAWINGS

FIG. 1 is a side perspective view of one embodiment of the electroblotting device, shown in a decoupled configuration.

Figure 2:
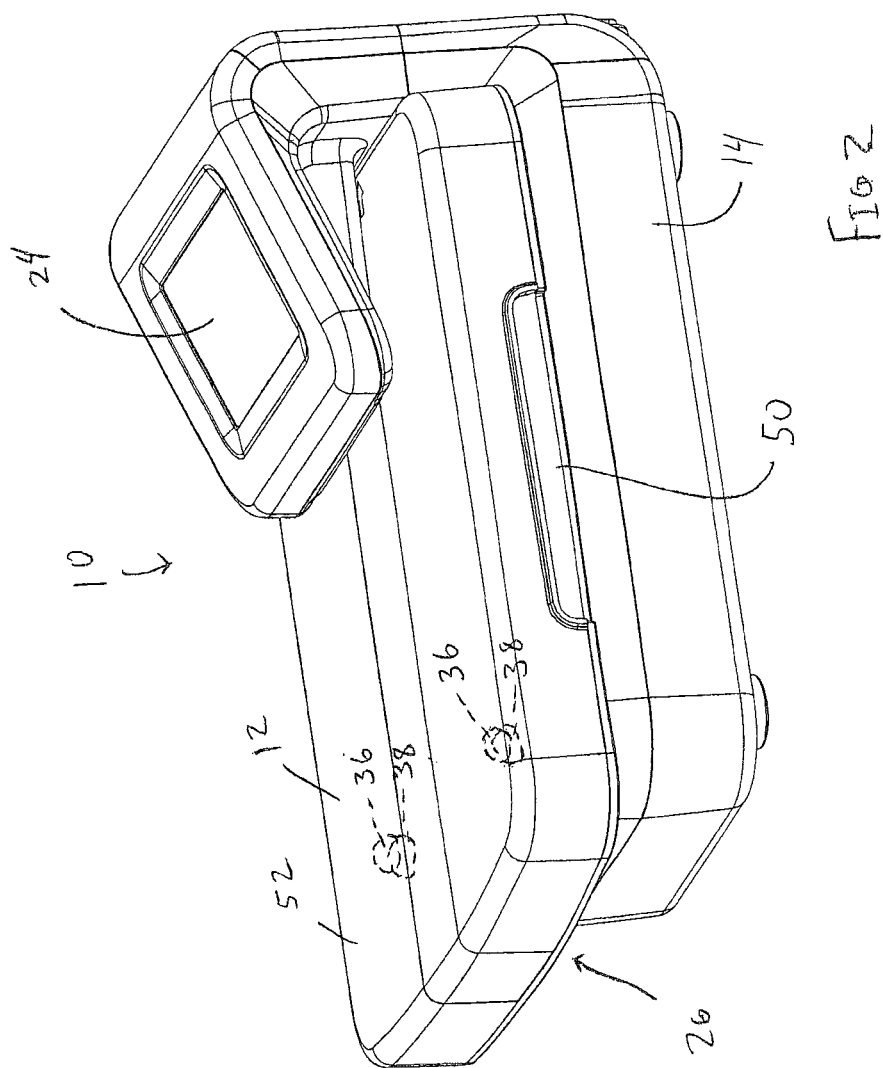
FIG. 2 is a side perspective view of the system of FIG. 1, shown in a coupled configuration.

One embodiment of an electroblotting device 10 is shown in FIGS. 1 and 2. The electroblotting device 10 can be used to transfer proteins or nucleic acids from a gel (e.g. following gel electrophoresis) or other material onto a membrane. The electroblotting device 10 can utilize a "semi-dry" electroblotting transfer technique in which a sandwich stack (including the gel and the membrane) is pre-wet with a transfer buffer, and electroblotting occurs between electrodes that are not submerged in a transfer buffer. The electroblotting provided by the device 10 is often utilized as a step in determining the presence and/or levels of certain proteins and/or nucleic acids.

The electroblotting device 10 can include, broadly speaking, a cassette 12 which is removably coupled to a base 14. The gel or other material impregnated with proteins and/or nucleic acids is loaded into the cassette 12. Filter papers, sponges or the like are inserted into the cassette 12 in a manner which will be described in greater detail below. The cassette 12 includes an anode 16 (FIG. 6) and a cathode 18 (FIG. 7) with the gel material and membrane positioned therebetween. The cassette 12 includes a pair of cassette electrical connectors 20 (FIG. 3) electrically coupled to the anode 16 and cathode 18. The base 14 includes a pair of corresponding base electrical connectors 22 (FIG. 1) configured to be electrically coupled to the cassette electrical connectors 20 to electrically couple the base 14 and the cassette 12 when the cassette 12 is connected to the base 14, as shown in FIG. 2. After the cassette 12 is properly loaded, the cassette 12 is then coupled to the base 14 such that the cassette 12 is in its home position wherein the cassette 12 is mechanically and electrically coupled to the base 14, as shown in FIG. 2.

The base 14 includes, or is electrically coupled to, a current source (not shown), such as a standard electrical outlet. The base 14 may also include a controller (not shown) that tracks and controls the flow of current through the device 10/cassette 12 and oversees/controls the electroblotting process. The base 14 may also include a user interface 24 which is operatively coupled to the controller. In the illustrated embodiment, the user interface 24 takes the form of a touch-sensitive screen that can receive inputs from, and provide outputs to, a user/operator of the electroblotting device 10.

In some cases, prior to commencing electroblotting, the user interface 24 may request inputs from the operator. Such inputs can include, for example, particular parameters of the electroblotting process, such as the size of the gel material (i.e. size and/or weight), the input voltage/current, the voltage/current desired to be applied to the gel material, etc. The user interface may also require the operator to actuate a "start" button or the like to initiate the electroblotting process.

Once the electroblotting process is initiated the base 14/current source applies a current to the cassette 12, via the contacts 20, 22, such as the current flows from the cathode 18 of the cassette 12, through the gel material and membrane, to the anode 16. The current flow causes proteins and/or nucleic acids carried in the gel to be deposited on the membrane. After the electroblotting process is complete (the timing of which can vary depending upon, for example, the size of gel, the particular electroblotting technique, amount of current applied, etc.) the membrane, with the proteins and/or nucleic acids attached thereto, is removed from the cassette 12 for further processing.

Figure 3:
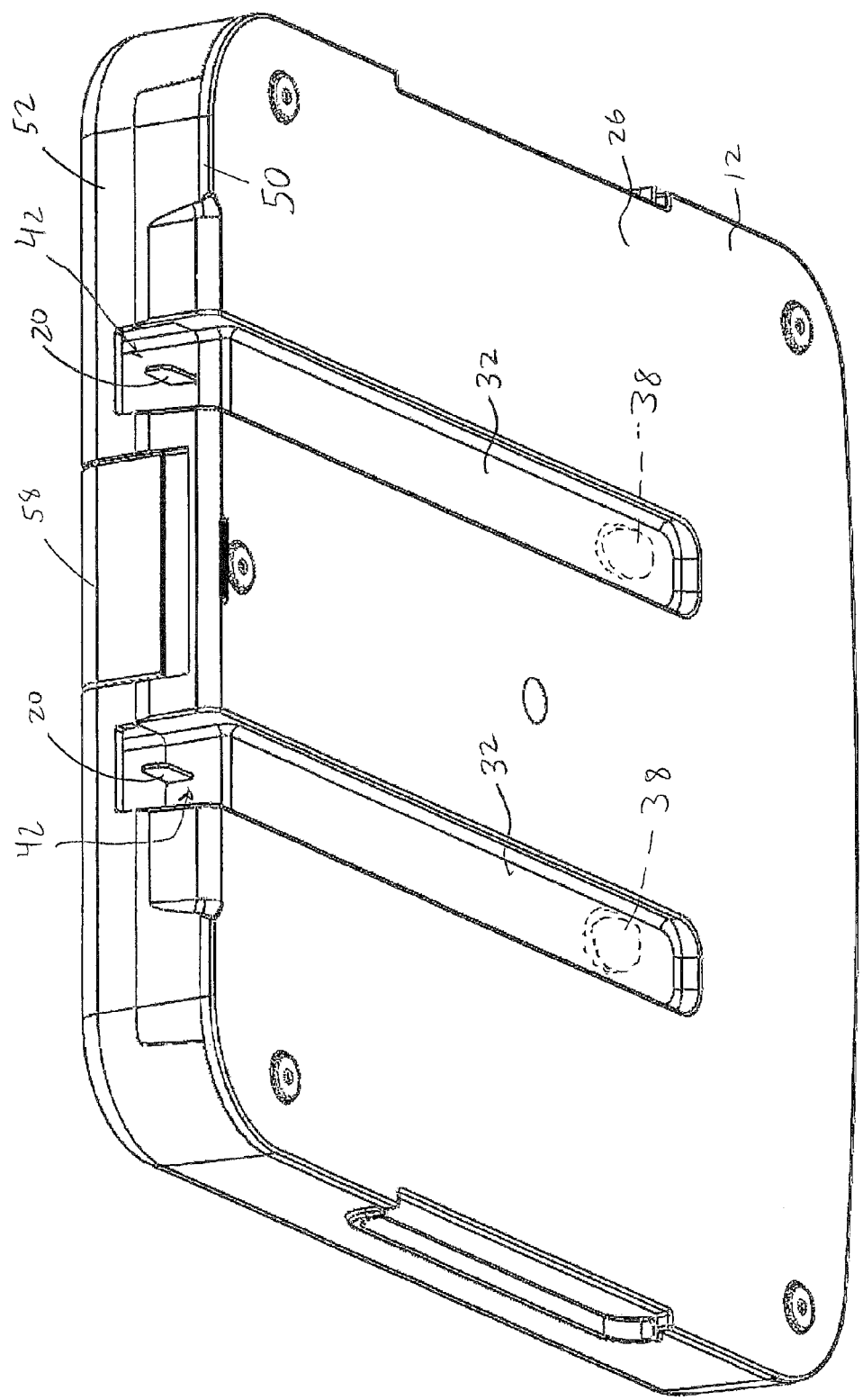
FIG. 3 is a bottom view of the cassette of the system of FIGS. 1 and 2.

As can be seen in comparing FIGS. 1 and 2 the cassette 12 is configured to be slidably coupled to the base 14 as the cassette 12 moves between its decoupled position (FIG. 1) to its coupled, or home position (FIG. 2). The cassette 12 includes a generally flat, planar lower surface 26 which slidably engages a generally flat, planar upper surface 28 of the base 14 when the cassette 12 is slidably moved. The base 14 includes a pair of raised, parallel and laterally spaced-apart rails 30 positioned on the upper surface 28 thereof. As shown in FIG. 3, the cassette 12 includes a pair of correspondingly shaped and positioned recesses or slots 32 on its lower surface 26 thereof, each which is configured to closely receive one of the rails 30 therein. The cassette 12 is configured to be slidably coupled to the base 14 in a sliding direction, where both the rails 30 and the slots 32 extend generally parallel to the sliding direction. In this manner, the rails 30 and slots 32 cooperate to guide the sliding motion of the cassette 12.

In the illustrated embodiment, the rails 30 extend the majority of the length of the upper surface 28 of the base 14 and, more particularly, at least about 50% of the length of the upper surface 28 of the base 14. Each slot 32 can extend the entire length, or at least about 50%, of the length of the lower surface 26 of the cassette 12. In this manner, the rails 30/slots 32 extend a sufficient length to ensure proper coupling and guidance of the cassette 12 during its sliding motion.

The illustrated embodiment shows the base 14 as having two rails 30 and the cassette 12 having two slots 32. However, the number of rails 30/slots 32 can be adjusted as desired, including use of only a single rail 30/slot 32 or more than two rails 30/slots 32. In addition, it should be understood that position of the rails 30 and slots 32 can be reversed. In particular, the rails 30 could be positioned on the lower surface 26 of the cassette 12, with the slots 32 being positioned on the upper surface 28 of the base 14. Further alternately, the cassette 12 can include both a rail 30 and a slot 32, with the base 14 including a corresponding slot 32/rail 30 configuration.

In the illustrated embodiment, each rail 30/slot 32 connector is laterally aligned with a connector 20, 22. This configuration can be particularly advantageous in that the lateral position of greatest alignment between the cassette 12 and the base 14 may be the lateral position where each rail 30 engages a slot 32. This positioning of the connectors 20, 22 thus helps to ensure proper alignment of, and electrical connection between, the connectors 20, 22.

As shown in FIG. 1, the base 14 may include a pair of components 36, such as magnets, coupled thereto and positioned below the top surface of the rails 30, or below the upper surface 28. As shown in FIG. 3, the cassette 12 may include a pair of components or magnets 38 positioned above the grooves 32, or above the lower surface 26. The magnets 36, 38 can be configured to be generally aligned such that, for example, a magnet 36 of the cassette 12 is positioned directly vertically above (i.e. aligned with) a magnet 38 of the base 14 when the cassette 12 is in its home/coupled positioned, as shown in FIG. 2.

The magnets 36, 38 help to provide tactile feedback to the operator of the electroblotting device 10. In particular, when the cassette 12 is manually coupled to the base 14, the user may be able to feel, hear and see positive engagement between the cassette 12 and the base 14 when the cassette 12 snaps into place in the home position. The attraction between the magnets 36, 38 may be sufficiently high that the movement/attraction is manually detectable, or may be sufficiently high that the cassette 12 can move solely due to magnetic forces when it sufficiently approaches the home position. In this manner, the user can be assured that the cassette 12 is properly positioned in its home position and ready for operation. In addition, the interaction between the magnets 36, 38 helps to retain the cassette 12 in place during the electroblotting process if the cassette 12 were to be inadvertently knocked, or other undesired forces applied thereto.

The interaction between the magnets 36, 38 also can provide feedback to the controller. In particular, the magnets 36, 38 may include and/or be coupled to a magnetic sensor/switch which can detect when the magnets 36, 38 are in sufficiently close proximity with each other. The switch can operate as an interlock to prevent the electroblotting process from being initiated (i.e. to prevent a current from being passed through the cassette 12) unless positive feedback is received that the cassette 12 is properly positioned in place.

FIGS. 1-3 illustrate the base 14 having a pair of magnets 36 and the cassette 12 including a pair of corresponding magnets 38. However, the number of magnets 36, 38 on the base 14 and cassette 12 can vary as desired. For example, the cassette 12 and base 14 may each include only a single magnet, or more than two magnets, etc. In addition, the magnets 36, 38 can be located at other positions besides the rails 30/slots 32. In one embodiment, each of the components 36, 38 takes the form of a permanent magnet (e.g. made of permanently magnetized or ferromagnetic material). However, if desired, one component 36, 38 in each component pair 36, 38 can take the form of a permanently magnetized material, and the other component 36, 38 in the pair can take the form of a magnetizable material, such as ferrous materials or the like. In addition, one or more of the components 36, 38 can take the form of electromagnets or electromagnetic material which do not provide a magnetic force unless a current is applied thereto.

Figure 4:
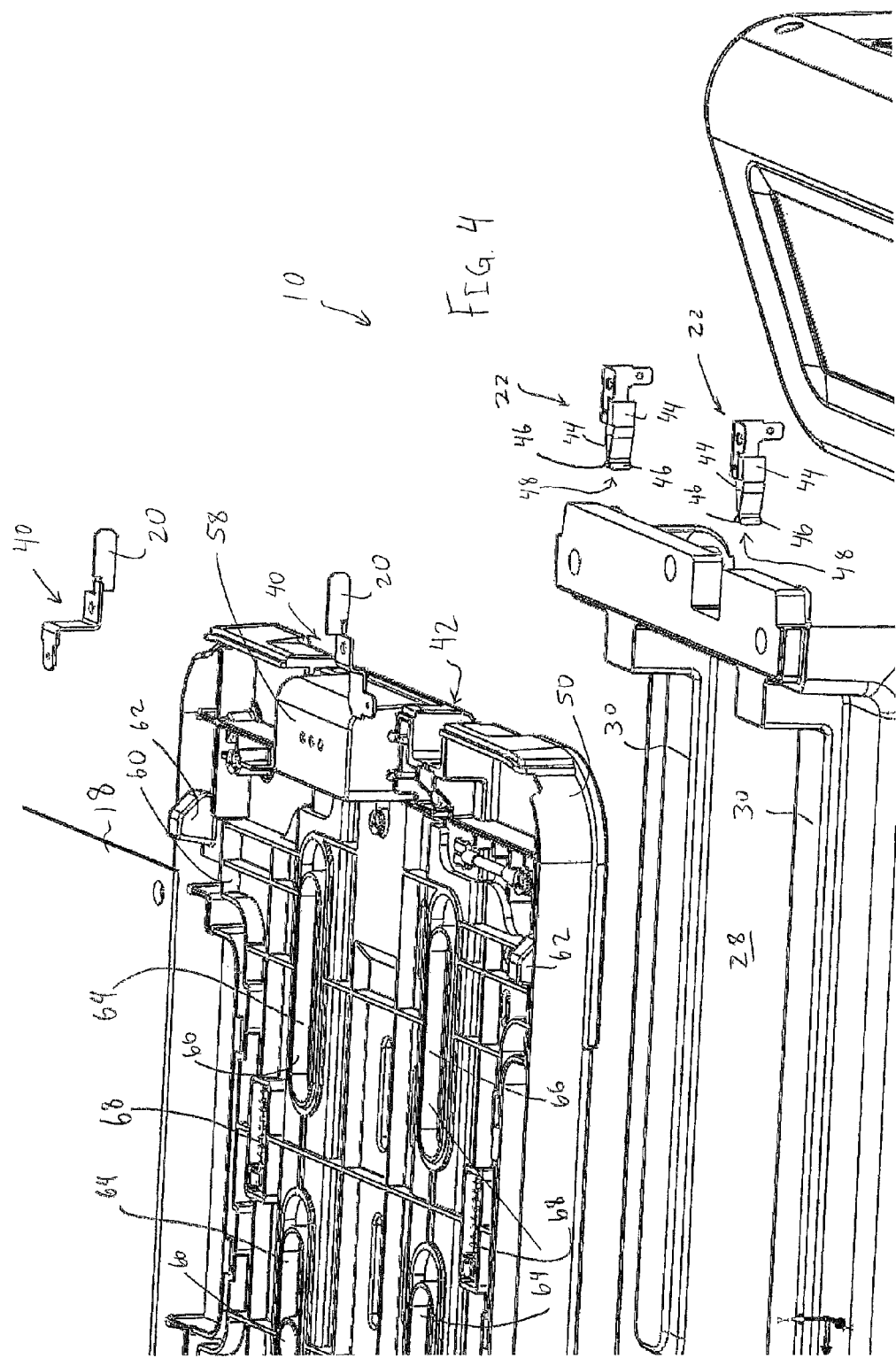
FIG. 4 is an exploded view of part of the device of FIG. 1.

As outlined above, the cassette 12 includes a pair of cassette electrical connectors 20 and the base 14 includes a pair of corresponding base electrical connectors 22 which are electrically coupled to the associated cassette electrical connectors 20 when the cassette 12 is in its coupled or home position. With reference to FIG. 4, one of the cassette electrical connectors 20 (the lower connector 20 in FIG. 4) is electrically coupled to the anode (not shown), and the other cassette electrical connector 20 (the upper connector 20 in FIG. 4) is electrically coupled to the cathode 18. In particular, in the embodiment of FIG. 4, the bottom illustrated cassette electrical connector 20 has a base portion 40 extending generally downwardly in a stepped manner to electrically couple to the anode, and the upper cassette electrical connector 20 has a base portion 40 extending generally upwardly in a stepped manner to electrically couple to the cathode 18. Each of the connectors 20, 22 can be made of an electrically conductive material, such as metal.

In one embodiment each of the cassette electrical connectors 20 takes the form of a male electrical connector having a generally blade-like flat, planar configuration. In the illustrated embodiment, each male/cassette connector 20 is generally oriented in a vertical plane when the cassette 12 is arranged in a horizontal plane and coupled to the base 14. As shown in FIG. 3, the cassette 12 can include a pair of recesses 42 in its end surface, and each cassette connector 20 is positioned in an associated recess 42 to generally protect the male connector. In one embodiment, each cassette electrical connector 20 is entirely recessed such that it extends forwardly a distance less than the depth of the recess 42.

As shown in FIG. 4, each of the base electrical connectors 22 take the form of female or alligator electrical connectors having a pair of female connector components 44 that are angled inwardly towards each other, each female connector component 44 including an outwardly-flared tip portion 46. Each female connector component 44 can be mounted in a moveable (e.g. cantilevered) manner and/or made of an elastically deformable material such that the female connector components 44 of a base electrical connector 22 are moveable apart or away from each other to accommodate an associated male connector 20 therebetween. The female connector portions 44 may include a gap 48 therebetween that, at its narrowest point, is narrower than the width of the associated male connector 20 to ensure sufficient mechanical contact therewith. Alternately, each female connector 20 may lack any gap such that the female connector components 44 engage each other when no male connector 20 is received therein.

Figure 5:
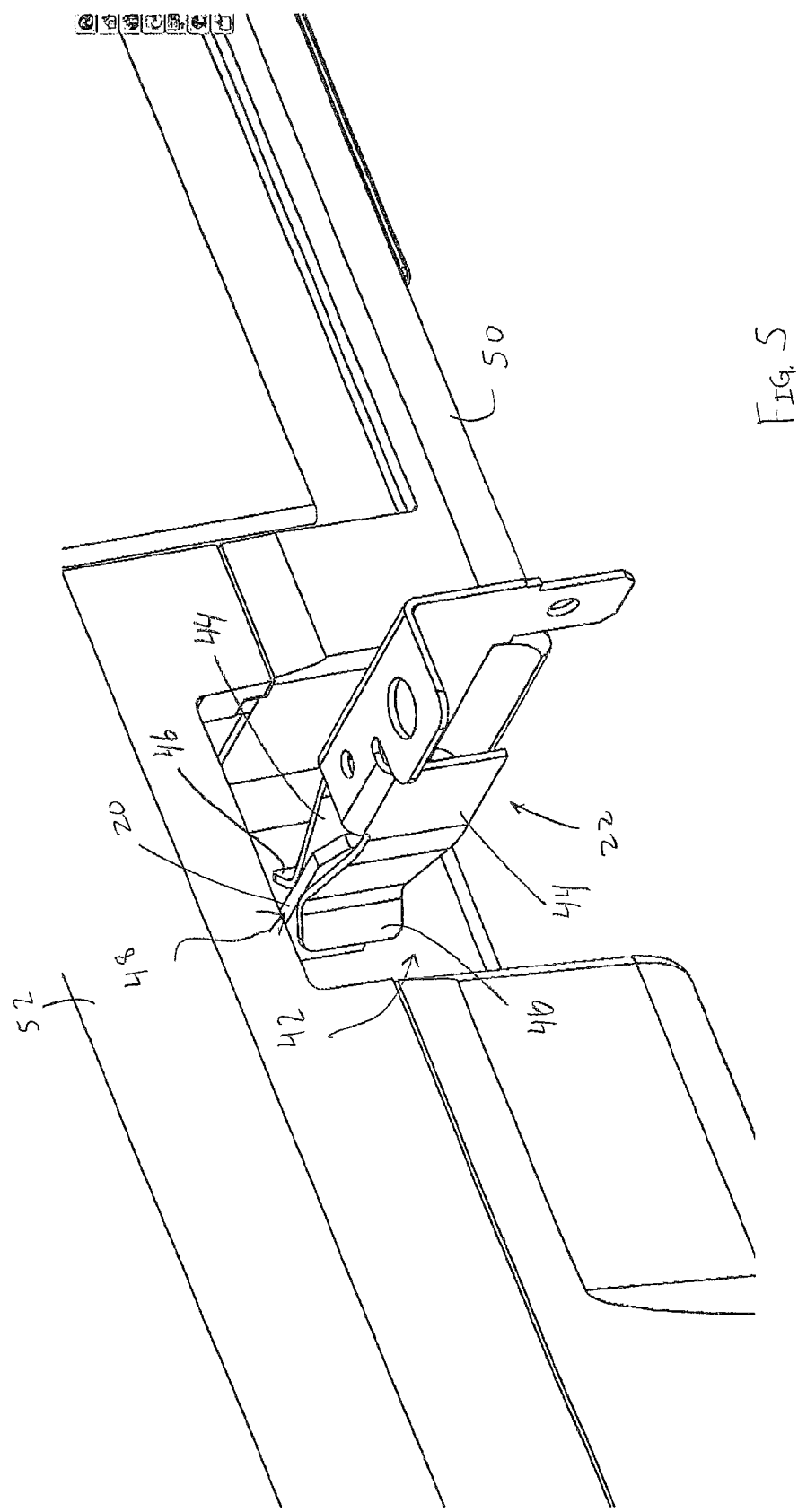
FIG. 5 is a rear perspective view illustrating interconnected electrical connectors of the base and the cassette.

In order to electrically couple the cassette 12 and the base 14, the cassette 12 is positioned on the base 14 and slid therealong until each male connector 20 slides between a pair of female connector components 44. Each male connector 20 is guided between the female connector components 44 by the outwardly-flared tip portions 46. The narrow gap 48 (if any) between the female connector components 44 ensures that each male connector component 20 electrically simultaneously engages both associated female connector components 44 to ensure strong electrical connection therebetween, as shown in FIG. 5. As outlined above, in one embodiment each connector 20, 22 is laterally aligned with the slots 32/rails 30, which can help to ensure proper alignment between the cassette electrical connectors 20 and base electrical connectors 22. Proper alignment and engagement between the connectors 20, 22 avoids electrical shorts and arcing, which can cause ineffective operation and/or heat build-up.

Once the cassette 12 is slid into place and the electrical connectors 20, 22 are engaged, the electroblotting process can be commenced. The electrical connectors 20, 22 can also provide some mechanical coupling between the cassette 12 and the base 14 in that the male connector components 20 can be frictionally gripped between the female electrical components 22 to secure the cassette 12 in place and provide mechanical resistance to its withdrawal. However, the cassette 12 can be mechanically secure in place by various other means, including but not limited to the magnetic engagement outlined above.

In the illustrated embodiment, the cassette 12 includes the male electrical connectors 20, and the base 14 includes female electrical connectors 22. However, this arrangement can be reversed. In particular, the female electrical connectors 22 could be positioned on the cassette 12, and the male electrical connectors 20 could be positioned on the base 14. Further alternately, the cassette 12 could include both a male 20 and a female 22 electrical connector, with the base 14 including a corresponding female/male configuration.

However, in one embodiment it may be useful for the male electrical connectors 20 to be positioned on the cassette 12. In particular, the cassette 12 can be separated from the base 14 and is more likely to be handled and manipulated, which means the cassette 12 may be expected to be exposed to more outside forces which could damage the electrical connectors 20. The female electrical connector 22 may need to be more precisely configured and include moveable parts, and therefore may need greater protection. Accordingly, by placing the female electrical connectors 22 on the base 14, the female electrical connectors 22 may be more protected, extending the useful life of the electroblotting device 10.

As outlined above, in one embodiment, each of the male components 20 is generally flat and planar and arranged in a vertical position (in one case, generally perpendicular to the plane of the cassette 12). As will be described in greater detail below, the cassette 12 can be separable into two separate cassette portions 50, 52 as shown, for example, in FIG. 6. Each of the cassette electrical connectors 20 can be coupled to separate portions 50, 52. The two portions 50, 52 in FIG. 6 can be secured back together but, due to imperfect couplings, or wear and tear, it is possible that the electrical connectors 20 may not always be properly aligned in the vertical direction when the cassette 12 is reassembled. However, by providing cassette electrical connectors 20 which extend generally vertically (parallel to movement of the cassette portions 50, 52 when they are joined), the connectors 20 accommodate greater tolerances and misalignment. However, the connectors 20, 22 need not necessarily be vertically arranged, and could instead be horizontally arranged, or positioned at an angle, etc.

Figure 6:
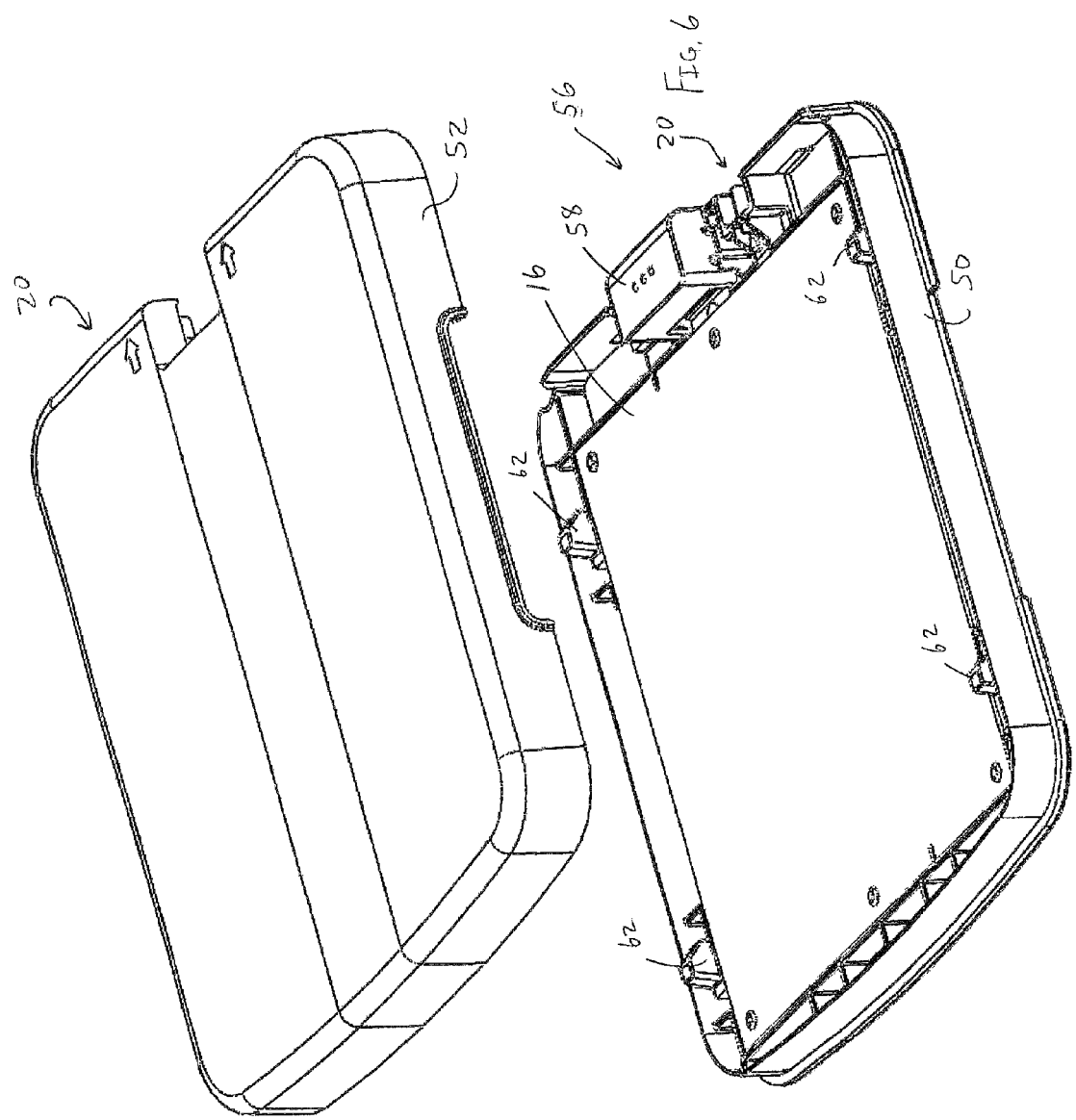
FIG. 6 is a partially exploded view of the cassette.

As outlined above, the cassette 12 is generally flat and planar, and includes two releasably attachable cassette portions 50, 52, each of which is also generally flat and planar, as shown in FIG. 6. As also noted above, one of the portions (the lower portion 50, in the illustrated embodiment) includes the anode 16 and the associated electrical connector 20, and the other portion (upper portion 52, in the illustrated embodiment) includes the cathode 18 and the associated electrical connector 20. Of course, the position of the anode 16 and cathode 18 can be reversed from the positions shown herein.

In order to prepare the cassette 12 for the electroblotting process, the first 50 and second portions 52 are separated, as shown in FIG. 6. A lower stack of materials, including components such as sponges and/or filter papers, is then placed on the anode 16/lower portion 50. The membrane or other material including the proteins and/or nucleic acids is then placed on top of the lower stack, and any trapped air bubbles may be removed by a blot roller or the like. Next, a gel material, such as a polyacrylamide gel, is placed on top of the membrane, and again any air bubbles may be removed with a blot roller. A top stack of materials, including filter paper and/or sponges, is then placed on top of the gel. The upper portion 52 is then placed on top of, and coupled to, the lower portion 50 such that the stacks, gel and material are trapped between the anode 16 and cathode 18.

Figure 7:
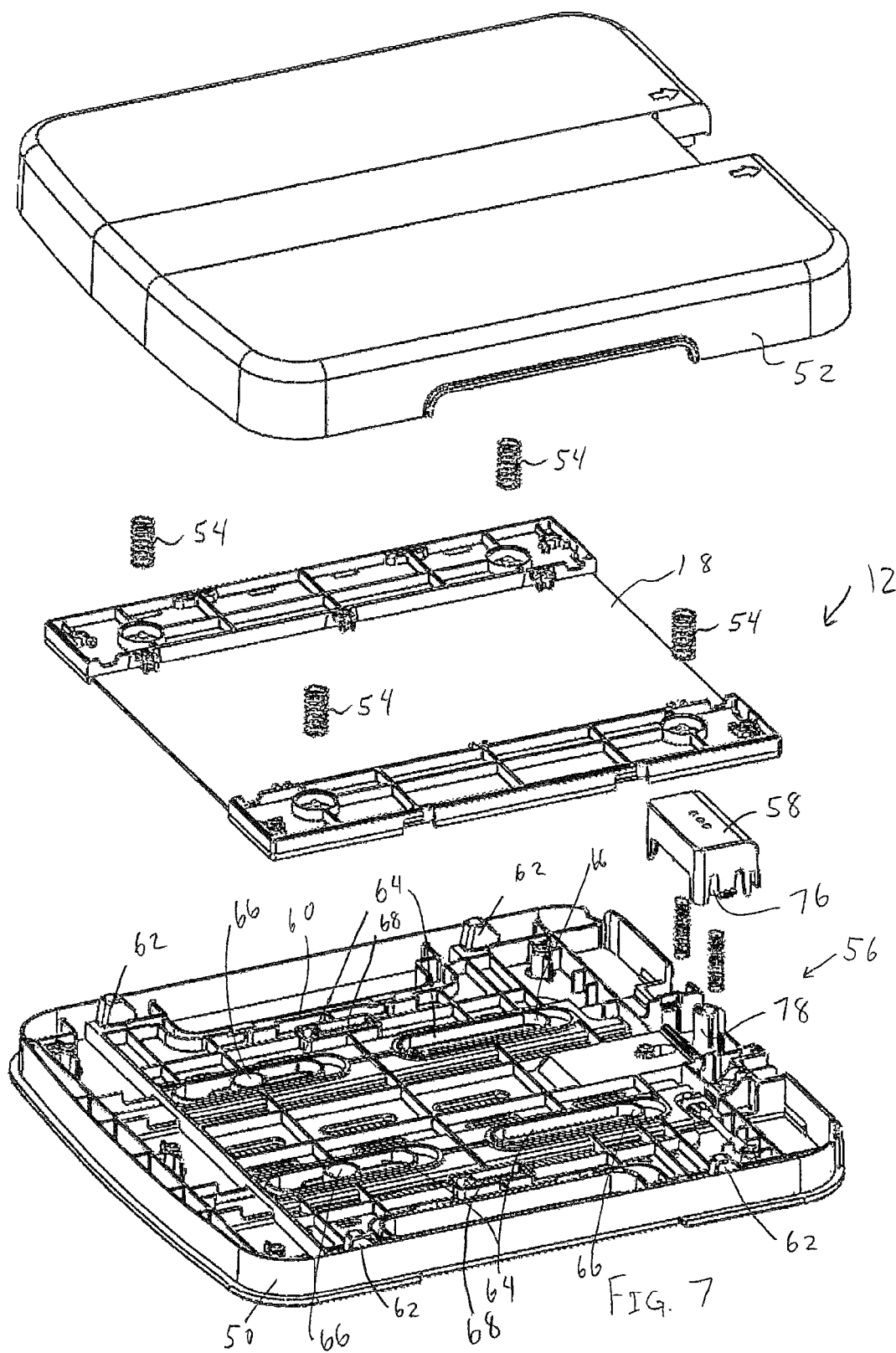
FIG. 7 is an exploded view of the cassette.

The anode 16 and the cathode 18 may be generally planar, parallel and spaced apart from each other. In one case, as shown in FIG. 7, a set of springs 54 are positioned between the cathode 18 and the body of the upper portion 52. The springs 54 are compressed when the cassette 12 is assembled, thereby spring biasing the cathode 18 downwardly into contact with the stack of materials to ensure proper electrical contact between the stack and the cathode 18. Once the cassette 12 is properly assembled, the electroblotting process can then continue in the manner outlined above.

The cassette 12 can include a coupling mechanism 56 configured to releasably couple the first 50 and second 52 portions, and an actuator 58 operatively coupled to the coupling mechanism 56. In particular, in one embodiment the lower portion 50 includes a plate 60 positioned in the lower portion 50, as shown in FIG. 7. The plate 60 can be positioned below the anode 16, which is not shown in FIG. 7 for illustrative purposes. The plate 60 is generally flat and planar, and includes a set of four protrusions 62 extending vertically upward therefrom and positioned about the anode 16, as shown in FIG. 6. The plate 60 is movable in its plane between an engaged positioned, in which the plate 60 is moved to the right in the embodiments of FIGS. 6-9, and a disengaged position in which the plate 60 is moved to the left in the embodiments of FIGS. 6-9.

As can be seen in FIG. 7, the plate 60 can include a plurality of slots 64 formed therein extending generally parallel to the direction of movement. The lower portion 52 can include a plurality of guides 66, wherein each guide 66 is positioned in an associated slot 64 to guide the lateral sliding movement of the plate 60. The plate 60 can be spring-biased to its forward (engaged) position by a set of springs 68.

Figure 8:
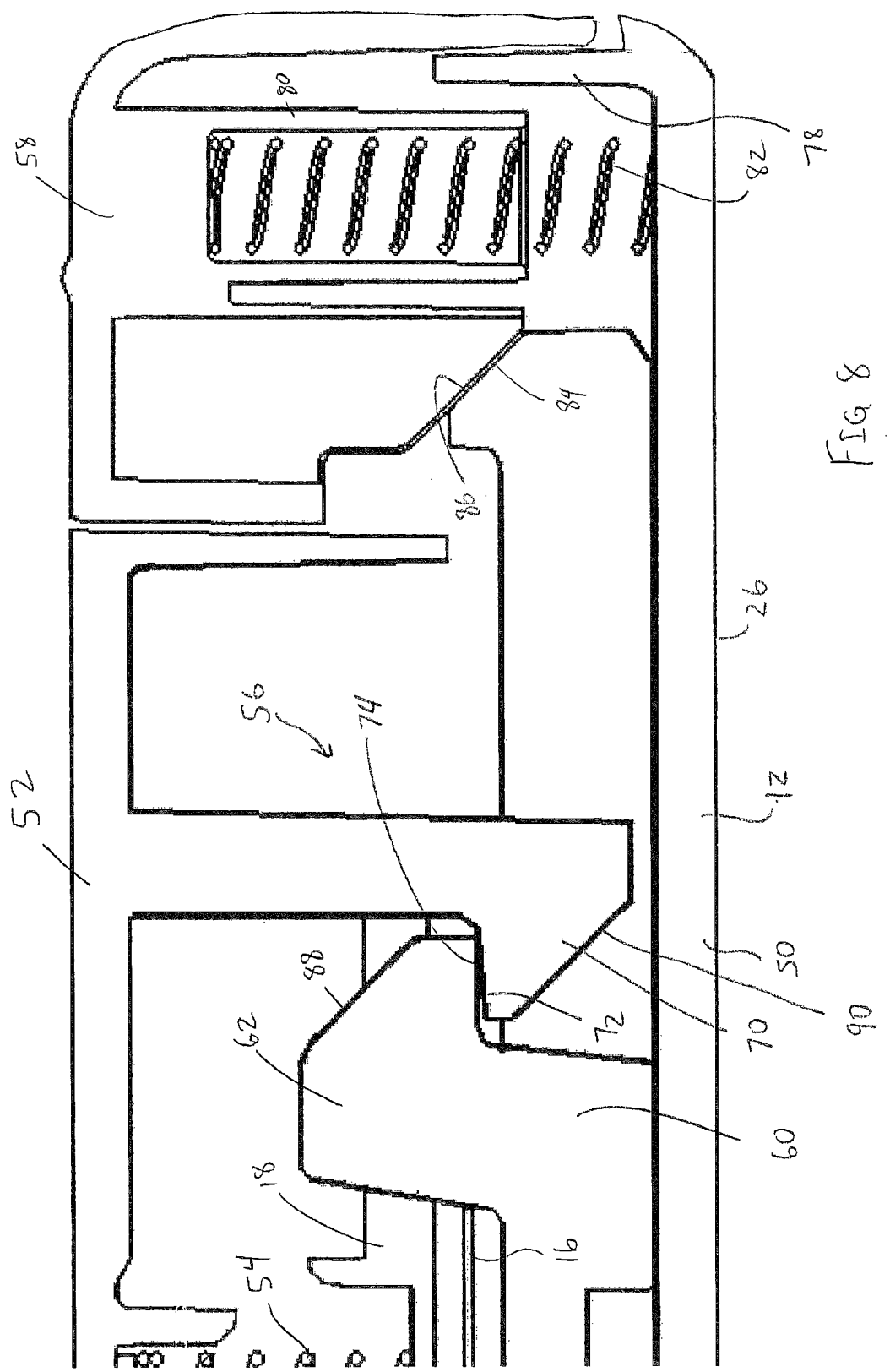
FIG. 8 is a detail side cross section of the cassette, with the button in a retracted position.
Figure 9:
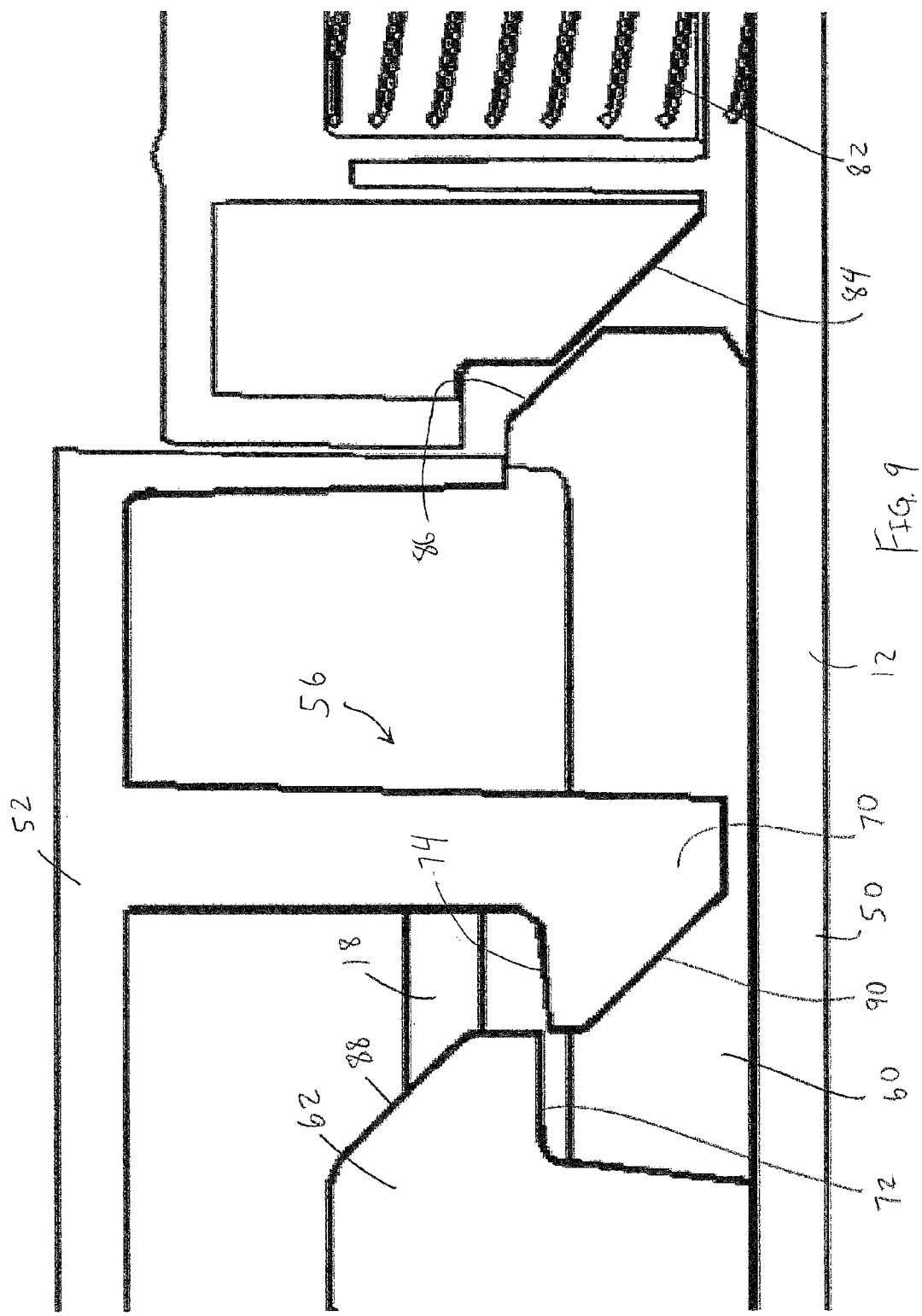
FIG. 9 is a detail side cross section of the cassette, with the button depressed.

The upper portion 52 can include a plurality of latches 70 carried thereon (see FIGS. 8 and 9). In the illustrated embodiment, the upper portion 52 includes four latches 70, each latch 70 corresponding to, and being aligned with, an associated protrusion 62. As shown in FIG. 8, each protrusion 62 includes a generally flat, planar lower surface 72, which lockingly engages a generally flat, planar upper surface 74 of a latch 70 when the portions are coupled together. In contrast, as can be seen in FIG. 9, when the plate 60 (and associated protrusions 62) are moved to the retracted position, each protrusion 62 is pulled laterally away from the associated latch 70 sufficiently that each latch 70 can be moved vertically upwardly, and the upper portion 52 separated from the lower portion 50.

In the illustrated embodiment, the cassette 12 includes an actuator 58 in the form of a manually depressible button which moves the plate 60 from its engaged to disengaged position to thereby release the upper portion 52 relative to the lower portion 50. In one embodiment, the button 58 is slidably coupled to a forward portion of the lower portion 50 and includes a downwardly-extending guide cylinder 70 which is received in an upwardly-extending cylinder 78 of the lower portion 50 (see FIG. 7) to guide the movement of the button 58 in a direction generally perpendicular to the plane of the cassette 12. As shown in FIGS. 8 and 9, the button 58 can also include a pair of generally cylinder spring-receiving components 80 positioned on either side of the guide cylinder 76. Each spring-receiving component 80 receives a spring 82 thereon to bias the button 58 to its upper position. The use of a pair of springs 82, on either side of the guide cylinder 76, helps to provide a smooth and balanced movement and biasing of the button 58.

As shown in FIGS. 8 and 9, the button 58 includes an angled camming surface 84 on a lower side thereof, and the plate 60 includes a correspondingly shaped and positioned angled camming surface 86 on an upper surface thereof. When the button 58 is moved downwardly or manually depressed, as can be seen in comparing FIGS. 8 and 9, the camming surface 84 of the button 58 engages the camming surface 86 of the plate 60, thereby causing the plate 60 to move (laterally to the left), thereby moving the protrusions 62 away from the latches 70. The upper portion 52 can then be lifted away from the lower portion 50. Once the manual actuation force is removed from the button/actuator 58, the button 58 returns to its upper/disengaged position, as urged by its springs 82, and the plate 60 returns to its forward/engaged position, urged by its springs 68, locking the upper 52 and lower 50 portions together.

Each protrusion 62 may also include an angled camming surface 88 on its upper surface thereof, and each latch 70 includes a corresponding camming surface 90 on its lower surface. In this manner, the upper 52 and lower 50 portions can be coupled together by simply placing the upper portion 52 on top of the lower portion 50 in the proper orientation such that the camming surfaces 88, 90 engage each other. Sufficient downward manual pressure applied to the upper portion 52 will then cause the plate 60 to retract to its disengaged position, allowing the latches 70 to snap into position below the protrusions 62. The plate 60 and protrusions 62 will then move to their engaged position, locking the upper 52 and lower 50 portions together.

It should be understood that the illustrated embodiment illustrates various configurations with respect to the button/actuator 58, latches 70, protrusions 62 and the like. However, the orientation of these various components can be varied as desired. For example, the plate 60/protrusions 62 can be located on the upper portion 52, the camming surfaces 84, 86, 88, 90 can differ in shape and orientation from that shown, etc. In addition, the illustrated embodiment shows four protrusions 62 with the four corresponding latches 70. However, the shape, number and configuration of the protrusions 62/latches 70 can be varied as desired. However, the use of multiple spaced apart coupling locations, as opposed to a single location, and can provide a more robust connection. The button/actuator 58 also allows for separation of the cassette 12 with a single motion, using a single hand. The dual spring design ensures smooth movement of the button 58, and further ensures that depressing the button 58 at any position therealong will allow separation of the cassette 12 such that the button 58 is not caught or hung-up during its movement, and also prevents partial separation of the cassette 12.

The cooperating slide devices, magnetic locking arrangement, improved electrical connectors and releasable cassette connection system provide a system that is robust, intuitive to use and provides superior operation.

Having described the invention in detail and by reference to the various embodiments, it should be understood that modifications and variations thereof are possible without departing from the scope of the claims of the present application.

What is claimed is:

1. An electroblotting system comprising:
  a cassette configured to receive a membrane and a material impregnated with at least one of proteins or nucleic acids, the cassette being slidably connectable to a base comprising a pair of raised, parallel and laterally spaced-apart rails positioned on an upper surface thereof, such that a current is passable through the cassette to cause at least some of said proteins or nucleic acids to be transferred from said impregnated material to said membrane, the cassette being generally flat and aligned in a plane and having:
    a first portion;
    a second portion configured to be releasably coupled to said first portion;
    a coupling mechanism configured to releasably couple said first portion to said second portion at multiple spaced apart coupling locations positioned on opposite outer edges of said first and second portions; and
  an actuator operatively coupled to said coupling mechanism such that manual operation of said actuator in a direction perpendicular to said plane causes said coupling mechanism to release said first portion relative to said second portion at each of said coupling locations.

2. The system of claim 1 wherein said coupling mechanism is configured to releasably couple said first portion to said second portion at multiple spaced apart coupling locations, and wherein said actuator is configured to, when depressed, cause said coupling mechanism to release said first portion at each of said coupling locations such that said first and second portions are entirely released and separable from each other by depressing said actuator.

3. The system of claim 1 wherein said coupling mechanism includes a plate included and positioned in said first portion, said plate being movable between an engaged position, in which said plate couples said first portion to the second portion, and a disengaged position in which said plate does not couple said first portion to said second portion, wherein said electroblotting system is configured such that depressing said actuator causes said plate to move from said engaged position to said disengaged position.

4. The system of claim 3 wherein said plate is generally flat and planar, defining a plane, and wherein said plate is configured to move in a direction of said plane when said plate moves between said engaged and said disengaged positions.

5. The system of claim 4 wherein said actuator is movable, when depressed, in a direction generally perpendicular to said plane.

6. The system of claim 3 wherein said plate is biased into said engaged position.

7. The system of claim 3 wherein said plate includes a plurality of protrusions, and wherein said second portion includes a plurality of latches, and wherein each protrusion is configured to engage a corresponding latch when said plate is in said engaged position, and wherein each protrusion is configured to not engage a corresponding latch when said plate is in said disengaged position.

8. The system of claim 1 wherein said actuator is a single component displaceable as a unit and movable between a depressed and an extended position, and wherein said actuator is biased into said extended position.

9. The system of claim 8 wherein said actuator is biased into said extended position by a pair of springs.

10. The system of claim 8 wherein said actuator includes at least one of protrusion or a recess, and wherein said cassette includes the other one of a protrusion or a recess, and wherein said protrusion is closely received in said recess to guide movement of said actuator between said depressed and said extended positions.

11. The system of claim 1 wherein said cassette includes an anode and a cathode and is configured such that said membrane and said impregnated material are positionable between said anode and said cathode such that said current is passable therethrough.

12. The system of claim 1 wherein one of said first or second portions includes an anode, and the other one of said first or second portions includes a cathode.

13. The system of claim 1 further comprising said base, wherein said base includes a current source operatively coupleable to said cassette when said cassette is coupled to said base.

14. The system of claim 13 wherein said membrane and said impregnated material are positioned in said cassette, and said cassette is attached to said base such a current is passed through the cassette to cause at least some of said proteins or nucleic acids of said impregnated material to be transferred from said impregnated material to said membrane.

15. A method for using an electroblotting system comprising:
 accessing a cassette that is generally flat aligned in a plane, the cassette having a first portion, a second portion and a coupling mechanism releasably coupling said first portion to said second portion at multiple spaced apart coupling locations positioned on opposite outer lateral edges of said first and second portions, the cassette further including an actuator operatively coupled to said coupling mechanism;
 manually operating said actuator by moving said actuator in a direction perpendicular to said plane to cause said coupling mechanism to release said first portion relative to said second portion at each of said coupling locations;
 positioning a membrane and a material impregnated with at least one of proteins or nucleic acids in said cassette;
 securing said first and second portions together; and
 connecting said cassette to a base comprising a pair of raised, parallel and laterally spaced-apart rails positioned on an upper surface thereof, such that a current is passable through the cassette to cause at least some of said proteins or nucleic acids to be transferred from said impregnated material to said membrane.

16. The system of claim 1, wherein the first portion of the cassette comprises a pair of parallel slots, laterally spaced apart and correspondingly shaped to the rails on a bottom surface thereof.

17. The system of claim 16, wherein the cassette is slidably coupled to the base guided by sliding motion of the slots and the rails, wherein the rails and the slots extend generally parallel to a sliding direction.

* * * * *